United States Patent
Park et al.

(10) Patent No.: US 10,286,750 B2
(45) Date of Patent: May 14, 2019

(54) APPARATUS FOR SIMULTANEOUSLY MEASURING INTERIOR TEMPERATURE AND FINE DUST IN VEHICLE

(71) Applicants: Hyundai Motor Company, Seoul (KR); Kia Motors Corporation, Seoul (KR)

(72) Inventors: June Kyu Park, Gyeonggi-do (KR); Dong Won Yeon, Hyeonggi-do (KR); Jong Sik Bae, Hyeonggi-do (KR); Jae Won Heo, Seoul (KR); Sang Yeop Lee, Jeollabuk-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 190 days.

(21) Appl. No.: 15/233,998

(22) Filed: Aug. 11, 2016

(65) Prior Publication Data
US 2017/0158020 A1    Jun. 8, 2017

(30) Foreign Application Priority Data

Dec. 2, 2015   (KR) .................. 10-2015-0170688

(51) Int. Cl.
*G01K 7/22*   (2006.01)
*B60H 1/00*   (2006.01)
(Continued)

(52) U.S. Cl.
CPC ........... B60H 1/00585 (2013.01); *G01K 7/22* (2013.01); *G01K 13/02* (2013.01); *G01N 15/06* (2013.01);
(Continued)

(58) Field of Classification Search
CPC ............ G01K 1/10; G01K 1/14; G01K 13/02; G01K 2201/02; G01N 25/00; G01N 1/2252; B05B 12/06; B05B 17/0623; B05B 1/083; B05B 3/02; B08B 2203/0288; B08B 3/026
(Continued)

(56) References Cited

U.S. PATENT DOCUMENTS

| 7,253,743 B2 * | 8/2007 | Liang ................... B01D 46/008 340/606 |
| 2005/0188686 A1 * | 9/2005 | Saito ....................... F01N 3/023 60/297 |

(Continued)

FOREIGN PATENT DOCUMENTS

| JP | H05240764 A | 9/1993 |
| JP | 2008-509802 A | 4/2008 |

(Continued)

*Primary Examiner* — Gail Kaplan Verbitsky
(74) *Attorney, Agent, or Firm* — Mintz Levin Cohn Ferris Glovsky and Popeo, P.C.; Peter F. Corless

(57) ABSTRACT

An apparatus is provided for simultaneously measuring interior temperature and fine dust in a vehicle. The apparatus measures interior temperature of a vehicle and fine dust in the air simultaneously by controlling flow rate of the interior air through a structure for changing air flow rate and making a division between a temperature sensing region and a dust sensing region based on a flow rate difference that occurs based on the structure for changing air flow rate.

8 Claims, 2 Drawing Sheets

(51) Int. Cl.
  *G01N 21/53* (2006.01)
  *G01K 13/02* (2006.01)
  *G01N 15/06* (2006.01)
  *G01N 21/3504* (2014.01)
  *G01N 21/15* (2006.01)

(52) U.S. Cl.
  CPC ............ *G01N 21/53* (2013.01); *G01N 21/534* (2013.01); *G01K 2013/024* (2013.01); *G01K 2201/02* (2013.01); *G01N 21/3504* (2013.01); *G01N 2015/0693* (2013.01); *G01N 2021/151* (2013.01); *G01N 2201/0686* (2013.01)

(58) Field of Classification Search
  USPC ................ 374/141, 7, 144, 208, 142, 148, 4
  See application file for complete search history.

(56) References Cited

U.S. PATENT DOCUMENTS

| | | | |
|---|---|---|---|
| 2006/0187070 A1* | 8/2006 | Liang | B01D 46/008 340/607 |
| 2017/0182447 A1* | 6/2017 | Sappok | F01N 11/00 |
| 2017/0234786 A1* | 8/2017 | Weber | G01M 15/102 73/23.33 |
| 2018/0023431 A1* | 1/2018 | Kubinski | F01N 3/027 |
| 2018/0052091 A1* | 2/2018 | Zhang | G01N 15/0656 |

FOREIGN PATENT DOCUMENTS

| | | |
|---|---|---|
| KR | 10-2001-0112571 A | 12/2001 |
| KR | 10-2004-0110412 A | 12/2004 |
| KR | 20-0394943 Y1 | 9/2005 |
| KR | 10-0539310 B1 | 12/2005 |
| KR | 2012-0022460 A | 3/2012 |

\* cited by examiner

APPARATUS FOR SIMULTANEOUSLY MEASURING INTERIOR TEMPERATURE AND FINE DUST IN VEHICLE

CROSS-REFERENCE TO RELATED APPLICATION

This application claims under 35 U.S.C. § 119(a) the benefit of priority to Korean Patent Application No. 10-2015-0170688 filed on Dec. 2, 2015, the entire contents of which are incorporated herein by reference.

BACKGROUND (a) Technical Field

The present disclosure relates to an apparatus for simultaneously measuring interior temperature and fine dust in a vehicle, and more particularly, to an apparatus for simultaneously measuring interior temperature of a vehicle and fine dust in the air by controlling a flow rate of the interior air.

(b) Background Art

A dust sensor used for a building or home is typically intended to detect the number of dust particles using a characteristic that various gas materials absorb light of certain wavelengths or scatter light. Such a dust sensor is provided with an additional heating device to generate air flow forcibly.

Meanwhile, for a vehicle, interior air flow in the vehicle is not as stable as that in the building or the house, a variation of the interior air flow occurs based on an air discharge amount and a mode of an air conditioner system, and irregular interior air flow may be generated by user operation such as opening or closing of a window during driving of the vehicle and the like. Therefore, when a conventional dust sensor configured to detect the number and concentration of particles of fine dust in a stable state of air flow is used (i.e., dust sensor for a building and a house), there is difficulty in applying the conventional sensor to a vehicle since accuracy and reliability are reduced. In this regard, since the conventional dust sensor may acquire valid measurement values in a stable state under which a variation of air flow is not severe, it may be difficult to apply such a conventional dust sensor to the vehicle in which unstable air flow occurs frequently.

The above information disclosed in this section is merely for enhancement of understanding of the background of the invention and therefore it may contain information that does not form the prior art that is already known in this country to a person of ordinary skill in the art.

SUMMARY

The present invention provides an apparatus for simultaneously measuring interior temperature and fine dust in a vehicle, which is capable of measuring interior temperature of a vehicle and fine dust in the air simultaneously by controlling flow rate of the interior air using a structure for changing air flow rate and forming a division between a temperature sensing region and a dust sensing region based on a flow rate difference that occurs based on the structure for changing air flow rate.

Accordingly, in one aspect, the present invention provides an apparatus for simultaneously measuring interior temperature and fine dust in a vehicle, that may include an enlarged tube section for changing air flow rate formed at the middle portion of a housing in an air flow direction, a temperature sensor configured to measure temperature, disposed at the forepart of the housing based on (e.g., relative to) the enlarged tube section and a dust sensor unit configured to detect fine dust, disposed at the backside of the housing based on (e.g., relative to) the enlarged tube section.

According an exemplary embodiment of the present invention, the enlarged tube section has a structure in which the inside diameter increases along the air flow direction, and also may have a helical structure on an inner peripheral surface of the enlarged tube section. The housing may include a blower fan disposed at the rear of the dust sensor to allow air to flow into the housing. Additionally, the blower fan may be disposed inside the housing with a rotating axis arranged in a straight line with the center line of an air inlet of the housing, and thus the blower fan may induce air flow in a longitudinal direction of the housing.

In addition, the dust sensing sensor unit may include: a light emitting unit configured to generate light; a light receiving unit configured to sense light emitted from the light emitting unit and scattered by fine dust; a lens unit configured to condense the light scattered by fine dust to the light receiving unit; and an infrared ray pass filter disposed between the lens unit and the light receiving unit to allow only the infrared ray of the light incident to the light receiving unit to pass through the filter.

According to a another exemplary embodiment of the present invention, in the dust sensor unit, the light emitting unit and the light receiving unit may be arranged within the housing to cause a moving direction of the light, which is emitted from the light emitting unit and then is incident onto the light receiving unit, to be formed in a direction intersecting with a flow direction of air within the housing. Further, in the dust sensor unit, the light emitting unit and the light receiving unit may be disposed to face each other with the lens unit interposed therebetween, the lens unit may be disposed at an open front end of a guard space portion disposed to protrude toward the outside of the housing, and the light receiving unit may be disposed at the inside rear end of the guard space portion.

Advantageous Effects

The apparatus for simultaneously measuring interior temperature and fine dust in a vehicle, according to the present invention, is capable of detecting fine dust in the interior of a vehicle, in which irregular air flow occurs, by generating steady air flow in the interior of the vehicle and, in particular, it is capable of simultaneously measuring the interior temperature of the vehicle and fine dust in the air by dividing a temperature sensing region and a dust sensing region based on a flow rate difference that occurs based on a structure for changing air flow rate in the inside of the housing.

BRIEF DESCRIPTION OF THE DRAWINGS

The above and other features of the present invention will now be described in detail with reference to exemplary embodiments thereof illustrated the accompanying drawings which are given hereinbelow by way of illustration only, and thus are not limitative of the present invention, and wherein.

Figure 1:
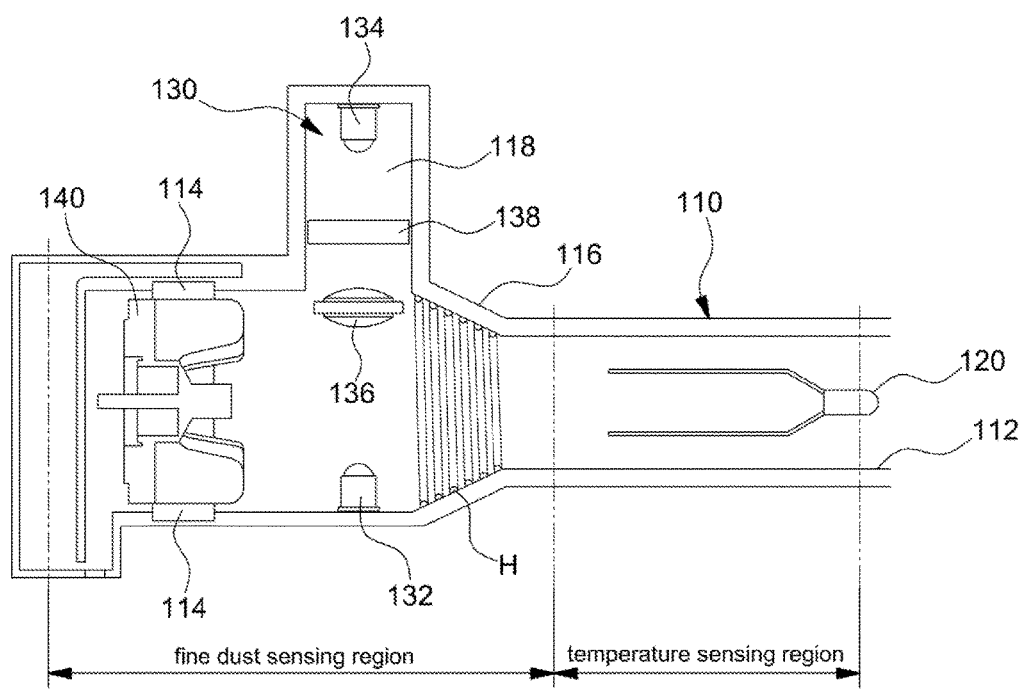
FIG. 1 is a configuration diagram illustrating an apparatus for simultaneously measuring interior temperature and fine dust in a vehicle, according to an exemplary embodiment of the present invention.

It should be understood that the appended drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment. In the figures, reference numbers refer to the same or equivalent parts of the present invention throughout the several figures of the drawing.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter reference will now be made in detail to various exemplary embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to an apparatus for more effectively measuring fine dust in the air of the interior of a vehicle, in which irregular air flow occurs frequently, and particularly to an apparatus for simultaneously measuring interior temperature and fine dust in a vehicle by applying a structure for changing air flow rate thereto.

Hereinafter, an exemplary embodiment of the present invention will be described with reference to accompanying drawings such that those skilled in the art may easily implement the invention. Reference will be made in detail to various exemplary embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other exemplary embodiments, which may be included within the spirit and scope of the invention as defined by the appended claims.

As shown in FIG. 1, an apparatus for simultaneously measuring interior temperature and fine dust in a vehicle, according to an exemplary embodiment of the present invention, may include a cylindrical housing 110; a temperature sensor 120 and a dust sensing unit 130 which are installed inside the housing 110; and a blower fan 140 configured to suction air forcibly into the inside of the housing 110.

In particular, the housing 110 may include an air inlet 112 for inflow of air in the interior of a vehicle at the opposite side of the blower fan 140 installed in the housing, and a plurality of air outlets 114 may be disposed on an outer peripheral surface surrounding the blower fan 140. The blower fan 140 may be disposed within the housing 110 and a rotating axis thereof may be arranged in a straight line with the center line of the air inlet 112, to force air to flow into the inside of the housing 110 by generating suction force and simultaneously control the flow rate of the air by generating steady air flow. The blower fan 140 may be disposed at the rear of both of the temperature sensor 120 and the dust sensor unit 130 to allow the air flowing forcibly into the inside of the housing 110 to pass through both of the temperature sensor 120 and the dust sensor unit 130.

The housing 110 may further include an enlarged tube section 116 for changing air flow rate at a central portion thereof based on an air flow direction formed by suction force of the blower fan 140 (or at the central portion in the longitudinal direction of the housing). The enlarged tube section 116 may be formed in a tapered structure in which the inner diameter increases gradually along the air flow direction in the housing 110 (or a front-to-rear direction, a longitudinal direction, etc.) while it has a helical structure formed on an inner peripheral surface thereof.

The housing 110 may be divided into a forepart (e.g., a front part) and a backside (e.g., a rear part) based on the enlarged tube section 116 having such a structure, for example, the forepart of the housing 110 may have an inner diameter which is about equal to the minimum diameter of the enlarged tube section 116 while the backside of the housing 110 may have an inner diameter which is about equal to the maximum diameter of the enlarged tube section 116.

The housing 110 allows the air flow rate at the forepart and the air flow rate at the backside to be different from each other since the internal space may be enlarged at the enlarged tube section 116, and accordingly air pressure may be decreased and thus the air flow rate may be reduced. In addition, the housing may inhibit forward fluidity of the air from being reduced due to decrease of air pressure at the enlarged tube section 116 since air flow rotating helically may be generated by the helical structure of the enlarged tube section 116. Accordingly, the housing 110 may form the air flow rate at the forepart relatively higher than the air flow rate at the backside and thus, the inside space of the housing 110 may be divided into a temperature sensing region and a fine dust sensing region based on the differential flow rate formed as above, wherein a temperature sensor 120 may be installed at the temperature sensing region to measure interior temperature of the vehicle and a fine dust sensor unit 130 may be installed at fine dust sensing region to measure fine dust in the air of the interior of the vehicle.

The temperature sensor 120 may be configured to measure temperature of air flowing into the forepart of the housing 110. The temperature sensor may include an element that operates as a sensor for converting thermal signal into electrical signal, such as a thermistor with an electrical property that resistance decreases as temperature increases, and the like. The temperature sensor 120 may be disposed at the central portion in a diametric direction at the forepart of the housing 110 and although not shown in drawings, the sensor may be supported fixedly within the housing 110 to prevent movement by the air flow.

The dust sensor unit 130 may be configured to detect fine dust in the air passing through the enlarged tube section 116 and then flowing into the backside of the housing 110 and may include a light emitting unit 132, a light receiving unit 134, and a lens unit 136. The light emitting unit 132 may be configured to generate light, wherein the light emitting unit 132 may include, for example, a light emitting device such as an infrared light-emitting diode (IR LED) and may be installed to be attached to the inner wall surface of the housing 110.

Additionally, the light receiving unit 134 may be configured to detect light emitted from the light emitting unit 132 and then scattered by fine dust in the air, wherein the light receiving unit 134 may include, for example, a light receiving sensor configured to receive and detect incident light and may be arranged on a substantially straight line with a predetermined distance at the opposite side of the light emitting portion 132. The lens unit 136 may be configured to condense light scattered by fine dust in the air to the light receiving unit 134, wherein the lens unit 136 may include, for example, a convergent lens such as a convex lens (or a condenser lens) having a thicker thickness at a central portion thereof and may be arranged to be supported fixedly between the light emitting unit 132 and the light receiving unit 134.

Further, arranged between the lens unit 136 and the light receiving portion 134 may be an infrared ray pass filter 138 configured to block visible light and ultraviolet ray among light incident onto the light receiving unit 134 and allow only the infrared ray to pass there through. The dust sensor unit 130 configured as described above may be configured to estimate the number and concentration of particles of fine dust with the aid of a microcomputer (not shown in drawings) connected thereto, based on output signal from the light receiving unit 134 configured to receive light emitted from the light emitting unit 132 and scattered by dust in the air and detect the light scattered by the dust.

In particular, the dust sensor unit 130 may be configured with the light emitting unit 132 and the light receiving unit 134 arranged within the housing 100 to cause a moving direction of the light, which is emitted from the light emitting unit 132, scattered by fine dust and then incident onto the light receiving unit 134, to be formed in a direction intersecting with a flow direction of air within the housing 110.

In other words, the dust sensor unit 130 may be configured to cause a moving direction of the light that moves between the light emitting unit 132 and the light receiving unit 134 to be perpendicular to a flow direction of air within the housing 110, wherein for the light receiving unit 134 to detect effectively fine dust in the air, a guard space portion 118 for accommodating the light receiving unit 134 may be provided at the backside of the housing 110.

The guard space portion 118 may be a space that is formed to protrude and extend toward the exterior at the backside of the housing 110 and to be connected with the inside space of the backside of the housing 110. In addition, the guard space portion 119 may be formed to protrude in a direction perpendicular to a flow direction of air within the housing 110 and extended in a moving direction of light between the light emitting unit 132 and the light receiving unit 134. The light receiving unit 134 disposed in the guard space portion may be arranged to face with the light emitting unit 132 with the lens 136 interposed therebetween. In particular, the lens unit 136 may be arranged at the front end side (i.e., open portion) of the guard space portion 118 and may allow the air passing through the enlarged tube section 116 to pass over between the lens unit 136 and the light emitting unit 132 of the dust sensor unit 130, to cause the light scattered by fine dust in the air to be converged by the lens unit 136 and impinged on the light receiving unit 134 arranged at the inside rear end of the guard space portion 118.

The dust sensor unit 130 may be configured to measure the number and concentration of particles in the air when the light receiving unit 134 detects the light emitted from the light emitting unit 132 and scattered by fine dust in the air. Accordingly, it may be possible to prevent the surface of the light receiving unit 134 from being contaminated by fine dust and the like by guiding the air flow within the housing 110 to form a constant flow path by virtue of air diffusion by the enlarged tube section 116 and air flow by the blower fan 140, and it may be possible to prevent the performance of detecting fine dust from being reduced due to surface contamination of the light receiving unit 134.

Figure 2:
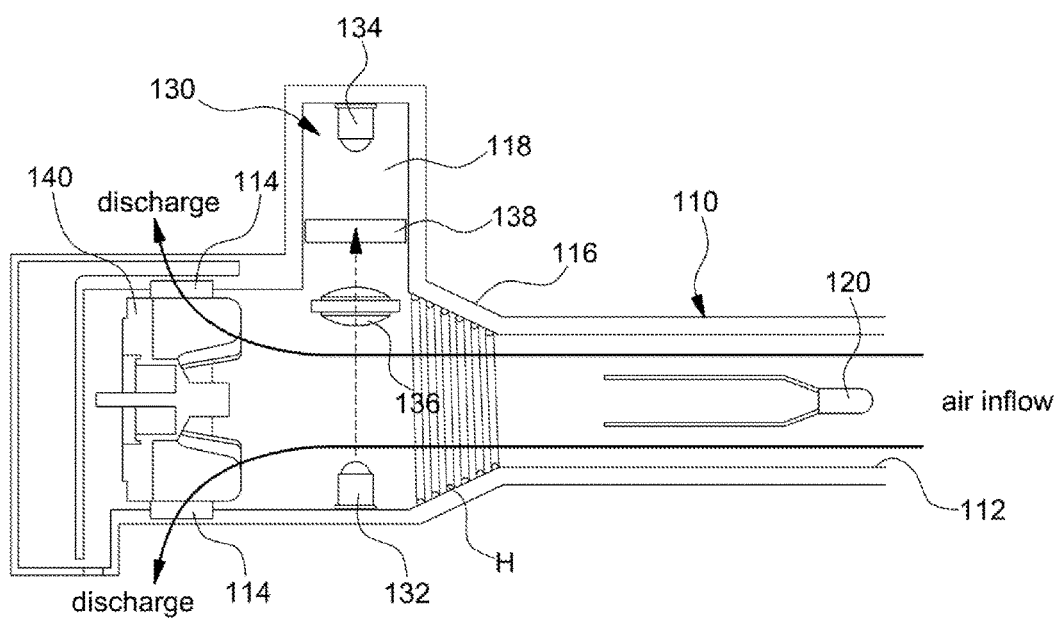
FIG. 2 is a schematic view showing an operating manner of the apparatus for simultaneously measuring interior temperature and fine dust in a vehicle, according to the exemplary embodiment of the present invention.

Referring to FIG. 2, in the apparatus of the present invention configured as described above, the temperature sensor 120 may be configured to measure interior temperature of a vehicle when air introduced through the air inlet 112 passes through the forepart (i.e., temperature sensing region) of the housing 110, while the dust sensor unit 130 may be configured to measure the number and concentration of particles of fine dust in the air when the air passes through the enlarged tube section 116 and then passes over the backside (i.e., fine dust sensing region) of the housing 110. Afterwards, the air may be discharged through air outlets 114 disposed proximate to the blower fan 140.

In addition, detection signals of the temperature sensor 120 (e.g., resistance values of a thermistor) and detection signals of the dust sensor unit 130 (e.g., detection values of a light-receiving sensor) may be input to a controller (not shown in drawings) mounted within a vehicle, and the controller may be configured to estimate the interior temperature of the vehicle and the number/concentration of particles of fine dust in the air based on signals input to the controller. For example, the controller as mentioned above may be a controller for an air conditioner system.

According to the present invention, it may be possible to simultaneously detect interior temperature of a vehicle and fine dust in the air by forming a flow rate (high speed) for allowing the temperature sensor 120 to detect interior temperature and a flow rate (low speed) for allowing the fine dust sensor unit 130 to detect fine dust relatively differentially by the structure (i.e., enlarged tube section) in which an air flow path within the housing 110 is enlarged.

The invention has been described in detail with reference to exemplary embodiments thereof. However, it will be appreciated by those skilled in the art that the scope of the present invention is not limited to the exemplary embodiments as mentioned above and that changes may be made in these exemplary embodiments without departing from the principles and spirit of the invention, the scope of which is defined in the appended claims and their equivalents.

What is claimed is:

1. An apparatus for simultaneously measuring interior temperature and dust in a vehicle, comprising:
    an enlarged tube section for changing air flow rate, formed at a middle section of a housing in an air flow direction;
    a temperature sensor configured to measure temperature within the vehicle and disposed at a forepart of the housing based on the enlarged tube section; and
    a dust sensor unit configured to detect dust and disposed at a backside of the housing based on the enlarged tube section,
    wherein the enlarged tube section has an inside diameter that increases along the air flow direction, and
    wherein the enlarged tube section has an inner peripheral surface having a helical structure.

2. The apparatus of claim 1, wherein the housing includes a blower fan arranged at a rear of the dust sensor unit to suction air into the housing.

3. The apparatus of claim 1, wherein the dust sensor unit includes:
    a light emitting unit configured to generate light;
    a light receiving unit configured to sense light emitted from the light emitting unit and scattered by fine dust; and
    a lens unit configured to condense the light scattered by fine dust to the light receiving unit.

4. The apparatus of claim 3, wherein the dust sensor unit is configured with the light emitting unit and the light receiving unit arranged within the housing to cause a moving direction of the light emitted from the light emitting unit and incident onto the light receiving unit to be formed in a direction intersecting with a flow direction of air within the housing.

5. The apparatus of claim 3, wherein the dust sensor unit is configured with the light emitting unit and the light receiving unit arranged to face each other with the lens unit interposed therebetween, the lens unit is arranged at an open front end of a guard space portion disposed to protrude toward an outside of the housing, and the light receiving unit is arranged at the inside rear end of the guard space portion.

6. The apparatus of claim 3, wherein the dust sensor unit includes an infrared ray pass filter disposed between the lens unit and the light receiving unit to allow only infrared ray of the light incident to the light receiving unit to pass through the filter.

7. The apparatus of claim 1, wherein the temperature sensor is fixedly supported fixedly within the housing to prevent movement by the air flow.

8. The apparatus of claim 3, wherein air outlets are disposed proximate to the blower fan and through which the air is discharged.

* * * * *